United States Patent
Reinhardt

(10) Patent No.: US 6,875,190 B2
(45) Date of Patent: Apr. 5, 2005

(54) ANKLE BRACE

(75) Inventor: Holger Reinhardt, Kempen (DE)

(73) Assignee: Bauerfeind AG, Zeulenroda (DE)

( * ) Notice: Subject to any disclaimer, the term of this patent is extended or adjusted under 35 U.S.C. 154(b) by 195 days.

(21) Appl. No.: 10/392,962

(22) Filed: Mar. 21, 2003

(65) Prior Publication Data

US 2004/0010214 A1 Jan. 15, 2004

(30) Foreign Application Priority Data

Mar. 22, 2002 (DE) .......................................... 102 13 238

(51) Int. Cl.⁷ ................................................ A61F 5/00
(52) U.S. Cl. ............................. 602/27; 602/13; 602/65; 128/882
(58) Field of Search ............................... 602/27, 13, 5, 602/6, 23, 65; 128/118.1, 882, 892, 893, DIG. 15, 894; 607/111

(56) References Cited

U.S. PATENT DOCUMENTS

| | | | |
|---|---|---|---|
| 4,977,891 A | | 12/1990 | Grim |
| 5,125,400 A | | 6/1992 | Johnson, Jr. |
| 5,209,722 A | * | 5/1993 | Miklaus et al. ............... 602/27 |
| 5,242,379 A | * | 9/1993 | Harris et al. .................. 602/27 |
| 5,250,021 A | * | 10/1993 | Chang .......................... 602/27 |
| 5,348,530 A | | 9/1994 | Grim et al. |
| 5,389,065 A | | 2/1995 | Johnson, Jr. |
| 5,489,259 A | | 2/1996 | Jacobs et al. |
| 5,620,411 A | * | 4/1997 | Schumann et al. ......... 128/882 |
| 5,630,792 A | * | 5/1997 | Neal ............................ 602/27 |
| 5,637,077 A | * | 6/1997 | Parker ........................... 602/6 |
| 6,056,713 A | * | 5/2000 | Hayashi ....................... 602/27 |
| 6,245,035 B1 | * | 6/2001 | Schrijver ..................... 602/27 |
| 6,602,215 B1 | * | 8/2003 | Richie, Jr. ................... 602/27 |
| 6,656,145 B1 | * | 12/2003 | Morton ....................... 602/27 |
| 6,749,578 B2 | * | 6/2004 | Peters ......................... 602/27 |

FOREIGN PATENT DOCUMENTS

| | | |
|---|---|---|
| DE | 306 226 | 3/1973 |
| DE | 2 238 961 | 2/1974 |
| WO | WO 91/07151 A1 | 5/1991 |
| WO | WO 98/08470 A1 | 3/1998 |

* cited by examiner

Primary Examiner—Fadi H. Dahbour
(74) Attorney, Agent, or Firm—Birch, Stewart, Kolasch & Birch, LLP

(57) ABSTRACT

Ankle brace with two arms extending over the ankle bones along the lower leg, said arms being joined under the foot by a flexible connecting member and being provided with cushioning chambers containing a fluid, each arm of the brace being provided with a single cushioning chamber with a longitudinal subdivision, said longitudinal subdivision forming a zone of reduced expandability in the region of the ankle bone and therefore forming opposite the ankle bone a recess which receives the latter, the connecting member being made of a material of such tensile elasticity that, during walking and the accompanying rolling of the foot as well as rhythmic pumping of the cushioning chambers, said connecting member is intermittently lengthened and shortened.

6 Claims, 4 Drawing Sheets

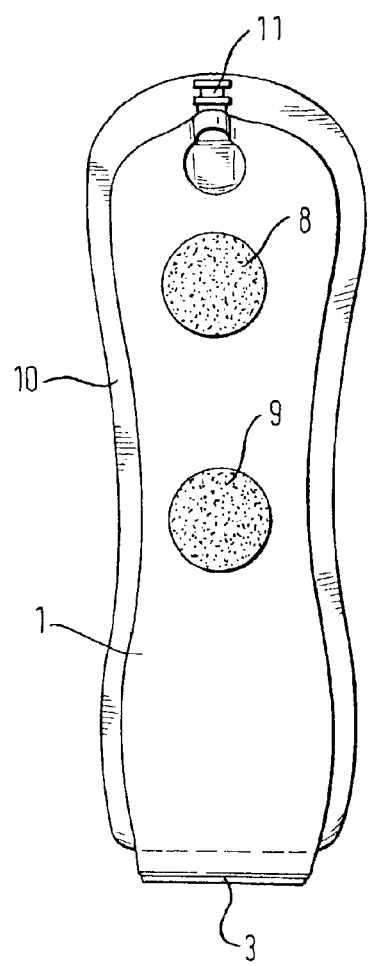
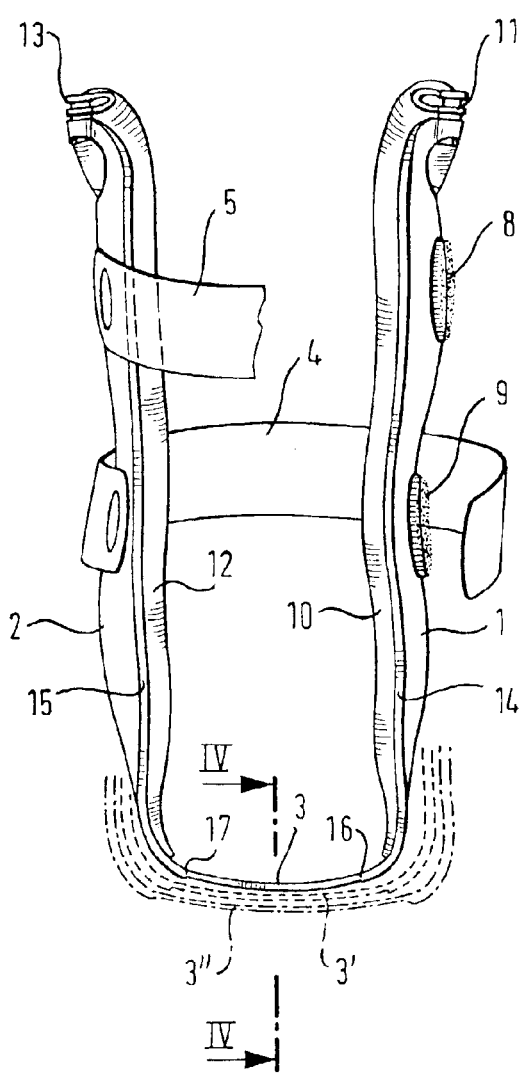

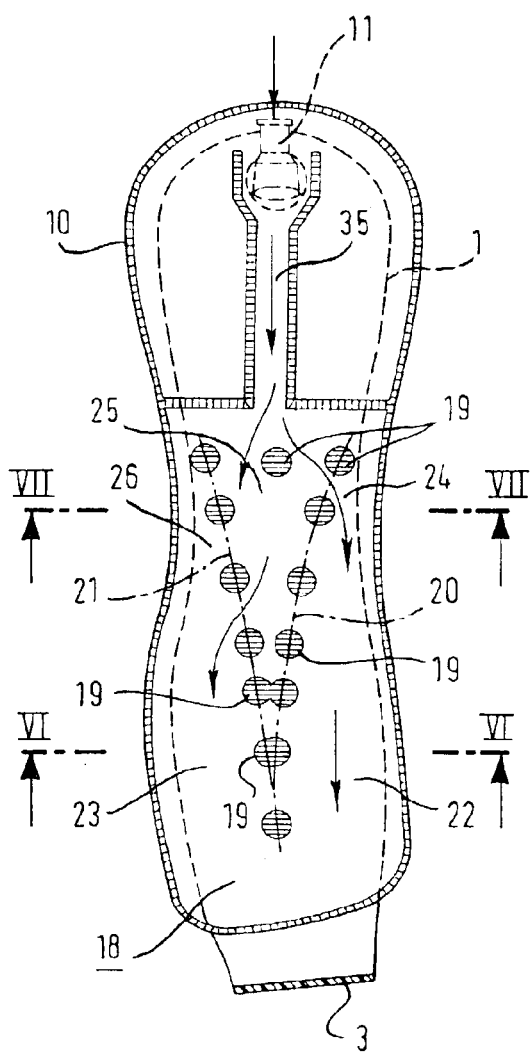
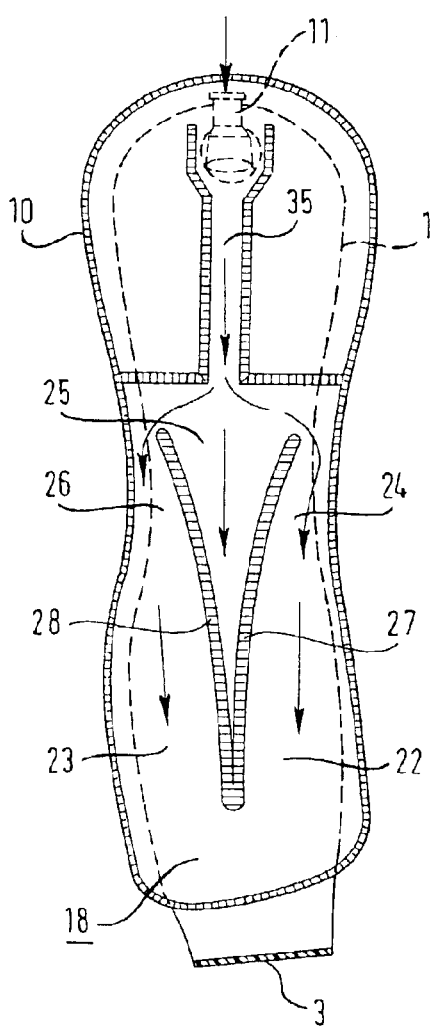

ANKLE BRACE

FIELD OF THE INVENTION

The invention relates to an ankle brace with two arms extending over the ankle bones along the lower leg, said arms being joined under the foot by a flexible connecting member and being provided with cushioning chambers containing a fluid.

BACKGROUND OF THE INVENTION

Such an ankle brace is presented and described in U.S. Pat. No. 5,125,400. More particularly, the said patent specification relates to ankle braces in which each arm of the brace has a plurality of cushioning chambers separately inflatable through their own valves, the two arms being joined by a simply flexible connecting member of Velcro material. Furthermore, the patent specification also refers to earlier ankle braces which had only one cushioning chamber on each arm. According to the information in the patent specification, however, the use of only one cushioning chamber resulted in high pressures outside the region of the ankle.

SUMMARY OF THE INVENTION

The object of the invention is to create an ankle brace with cushioning chambers containing a fluid, in which ankle brace the ankle bone is subjected to an especially low pressure and in which, moreover, during walking, the associated rhythmic pressure action on the cushioning chambers results in a decreasing surface pressure towards the knee, this promoting the draining of blood from the ankle. The latter is of importance especially with regard to the treatment of swelling in the region of the ankle.

The object of the invention is achieved in that each arm of the brace is provided with a single cushioning chamber with a longitudinal subdivision, said longitudinal subdivision forming a zone of reduced expandability in the region of the ankle bone and therefore forming opposite the ankle bone a recess which receives the latter, and in that the connecting member is made of a material of such tensile elasticity that, during walking and the accompanying rolling of the foot as well as rhythmic pumping of the cushioning chambers, said connecting member is intermittently lengthened and shortened.

This ankle brace according to the invention results first of all in the advantage of simplified manufacture, because the ankle brace requires only one cushioning chamber for each arm of the brace, with the result that also only one inlet valve is required for each cushioning chamber. Despite the use of only a single cushioning chamber for each arm of the brace, the desired difference in surface pressure is achieved in that each cushioning chamber has a longitudinal subdivision which creates the zone of reduced expandability in the region of the ankle bone, because, as a result of the longitudinal subdivision, the cushioning chamber forms in that region a recess into which the ankle bone is able to project in relatively pressure-free manner. The function of the cushioning chambers is especially exploited during walking and the accompanying rolling of the foot, namely in that this permits the rhythmic pumping of the cushioning chambers in that the connecting member joining the two arms of the ankle brace is made of a material of tensile elasticity. During walking, the connecting member is able more or less rhythmically to expand and contract, this effecting a corresponding pumping of the cushioning chambers without this resulting in particularly high pressure fluctuations, which are extensively compensated by the tensile elasticity of the expanding and contracting connecting member.

The longitudinal subdivision is established in easy-to-manufacture manner by connections disposed between opposite walls of said cushioning chamber, said connections extending along the longitudinal subdivision. According to currently prevailing technology, said connections are advantageously formed by welding. It is also pointed out, however, that the connections may also, of course, be established, for example, by glueing.

A simple design of the connections results in that said connections are formed by series-arranged spot welds. Conversely, it is also possible for the connections to be formed by weld seams.

An especially advantageous design of the longitudinal subdivision is achieved in that, for its realization, two lines of connections are provided, said lines extending in a V-shape such that the two lines meet in the region of the ankle bone and splay so wide apart towards the knee that, starting from the region of the ankle bone, two subchambers are formed next to the ankle bone and three juxtaposed subchambers are formed in the transition of the lines towards the knee, the cross section of said three juxtaposed subchambers in the inflated state being decreasingly smaller than the cross section of each of the two subchambers in the region of the ankle bone.

With this design of the connections, there are in effect in the region of the ankle bone two subchambers situated next to the ankle bone and three juxtaposed subchambers in the further region of the arms of the brace in the transition of the lines towards the knee, said subchambers all being part of the single cushioning chamber of each arm of the brace and therefore being inflated when the cushioning chamber is inflated and also being able to equalize each other with regard to their internal pressure towards the entire region of the cushioning chamber. This design results, next to the ankle bone, in a region with two larger subchambers and, in the region at the end of the "V" formed by the connections, in three juxtaposed subchambers the cross section of which in the inflated state is smaller than the cross section of the two subchambers in the region of the ankle bone. When, therefore, during walking, a pumping effect is exerted on the two subchambers in the region of the ankle bone, this effect gives rise to a pressure in the direction of the three subchambers in the region of the end of the V, where, however, owing to the distribution of the pressure over the three subchambers, the surface pressure on the leg of the wearer decreases. The fact that the two lines meet in the region of the ankle bone and splay so wide apart towards the knee means that, starting from the region of the ankle bone, two subchambers are formed next to the ankle bone and three juxtaposed subchambers are formed in the transition of the lines towards the knee, the cross section of said three juxtaposed subchambers in the inflated state being decreasingly smaller than the cross section of each of the two subchambers in the region of the ankle bone, with the result that this considerably facilitates the draining of the blood from the region of the ankle bone. This effect is made possible in particular also by the fact that, because of its tensile elasticity, the connecting member joining the two arms of the ankle brace under the foot is able to expand and contract again during walking.

BRIEF DESCRIPTION OF THE DRAWINGS

An example embodiment of the invention is presented in the drawings, in which:

FIG. 2 shows the same ankle brace in a top view of the shinbone;

FIG. 3 shows the design according to FIG. 2 rotated through 90°;

FIG. 4 shows a cushioning chamber in section with connections formed by spot welds;

FIG. 5 shows a cushioning chamber in section with connections formed by weld seams;

DETAILED DESCRIPTION OF THE DRAWINGS

Figure 1:
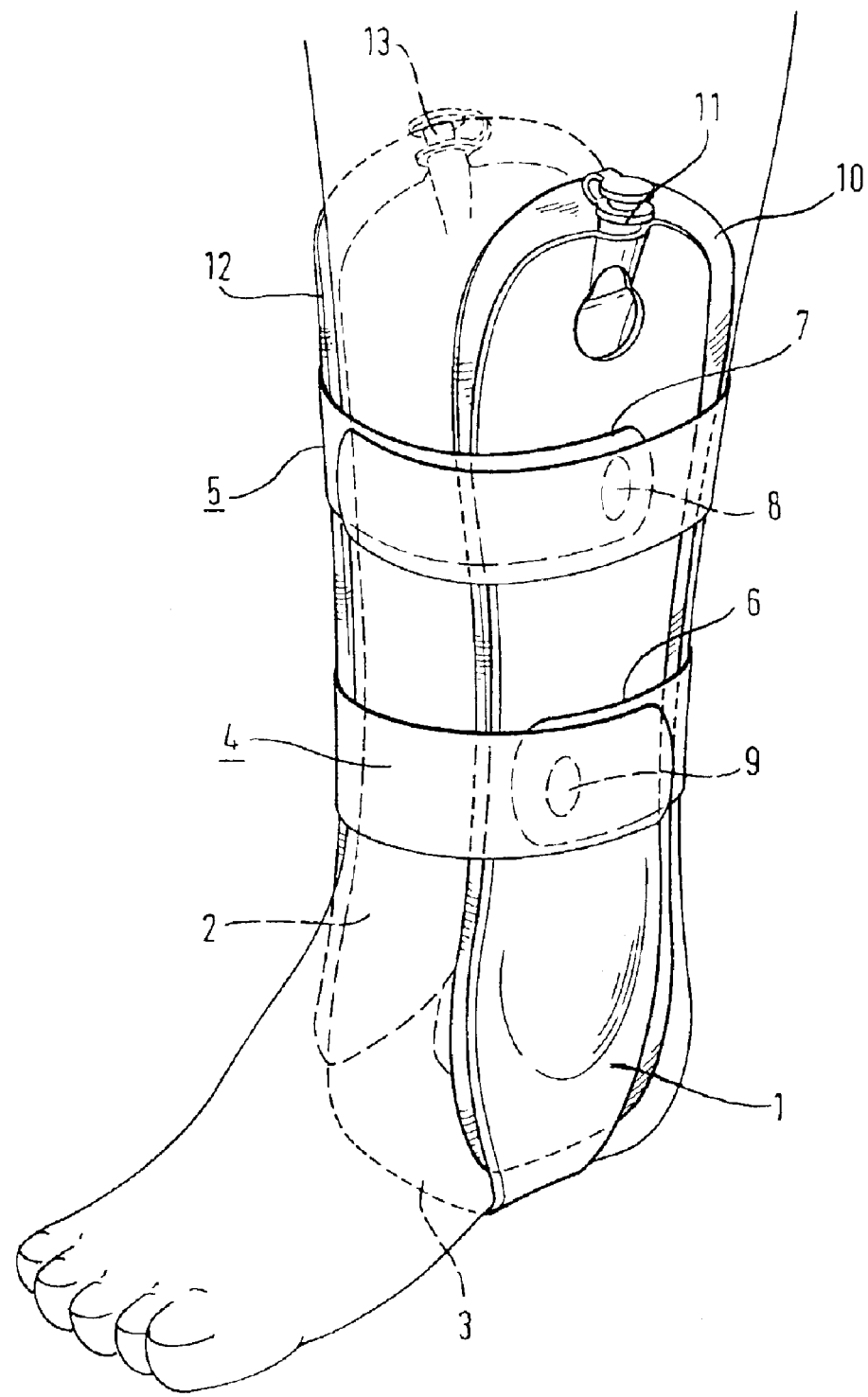
FIG. 1 shows a perspective view of an ankle brace fitted to a left foot.

The ankle brace fitted to a foot in FIG. 1 comprises the two arms 1 and 2 which extend from the sole of the foot towards the knee and which are joined in the region of the sole of the foot by the connecting member 3 (invisible in FIG. 1). The design and function of the connecting member 3 will be discussed in greater detail in connection with FIG. 2. The ankle brace with its two arms 1 and 2 is fixed in place by the two tapes 4 and 5 which are fixed to the arm 2 and which overlap in the region of the arm 1. The bottom parts 6 and 7 are furnished with Velcro parts 8 and 9 which interact in known manner with corresponding parts on the inner sides of the overlapping ends of the tapes 4 and 5. This manner of fixing of an ankle brace equipped with two arms is known.

The arm 1 is joined to the continuous cushioning chamber 10 which, with the ankle brace fitted, lies between the arm 1 and the leg of the wearer. The cushioning chamber 10 is inflated via the valve 11 which is of known design. Instead of air for inflating the cushioning chamber 10, it is, of course, also possible to use a different fluid; however, it should be pointed out that, for the purposes described here, it is primarily air which is a suitable medium. The arm 2 on the other side of the leg carries the cushioning chamber 12 which is inflated via the valve 13. To that extent, therefore, there is a mirror image of the arm 1 and cushioning chamber 2.

FIG. 2 shows the ankle brace from FIG. 1 in a top view of the shinbone of the wearer, with the result that the two arms 1 and 2 are directly visible with their edges 14, 15. The arms 1 and 2 are joined in the region of the sole of the foot, as already described in connection with FIG. 1, by the connecting member 3 which is made of a material of tensile elasticity. The arms 1 and 2 have the edges 14 and 15 which transition into the connecting member 3. As can be seen, the connecting member 3 itself is thinner than the edge 14 or 15, this being apparent at the two weakening points 16 and 17 in the region of the transition of the connecting member 3 into the arms 1 and 2. The material of the connecting member 3 may be, for example, a thermoplastic elastomer which transitions into the material of the arms 1 and 2 via the two weakening points 16 and 17. The consequence of this design is to allow the arms 1 and 2 easily to be forced apart laterally in the region of the sole of the foot during walking and rolling of the foot in that, namely, the connecting member 3 yields in suitably tensile elastic manner, this being indicated by the two broken-line arrangements in the region of the connecting member 3, identified by the regions 3' and 3".

FIG. 3 shows the ankle brace from FIG. 2 rotated through 90°, the arm 1 facing and being visible to the observer. FIG. 3 clearly shows that, as viewed by the observer, disposed behind the arm 1 is the cushioning chamber 10 which, consequently, is in contact with the leg of the wearer.

FIG. 4 shows a section along line IV—IV from FIG. 2, the connecting member 3 therefore being shown in section. Accordingly, the representation in FIG. 4 shows the observer the inside of the cushioning chamber 10 with its valve 11 and, behind it (shown by the broken line), the arm 1. The cushioning chamber 10 contains the single chamber space 18 into which air is blown via the valve 11 and the channel 35. The channel 35 is formed by correspondingly positioned welds seams. Provided in the region of the chamber space 18 is a longitudinal subdivision, formed by series-arranged spot welds 19 which are here disposed in the form of a "V" and which lie on the lines 20 and 21 (shown by dash-dotted lines). Owing to the said subdivision, two subchambers 22 and 23 are formed by the longitudinal subdivision in the region of the ankle bone, where the two lines 20 and 21 meet, and, because of the V-shape of the two lines 20 and 21, three subchambers 24, 25 and 26 are formed in the upper region of the ankle brace. As can be seen, the cross section of said subchambers continuously decreases in the inflated state from the subchambers 22, 23 to the subchambers 24, 25, 26, the consequence of which is that, when the cushioning chamber 10 is inflated with its single chamber space 18, this results in an upwardly decreasing surface pressure. The ankle bone is situated approximately where the lines 20 and 21 meet, with the result that it is possible at this point for a recess formed by the spot welds 19 to act as a pressure relief for the ankle bone, this being discussed in greater detail in connection with FIG. 6.

FIG. 5 shows a variant of the representation in FIG. 4, this variant consisting in that, in this case, the series-arranged spot welds 19 are formed by the two welds seams 27 and 28, which ultimately have the same effect as the spot welds 19 situated on the lines 20 and 21.

Figure 6:
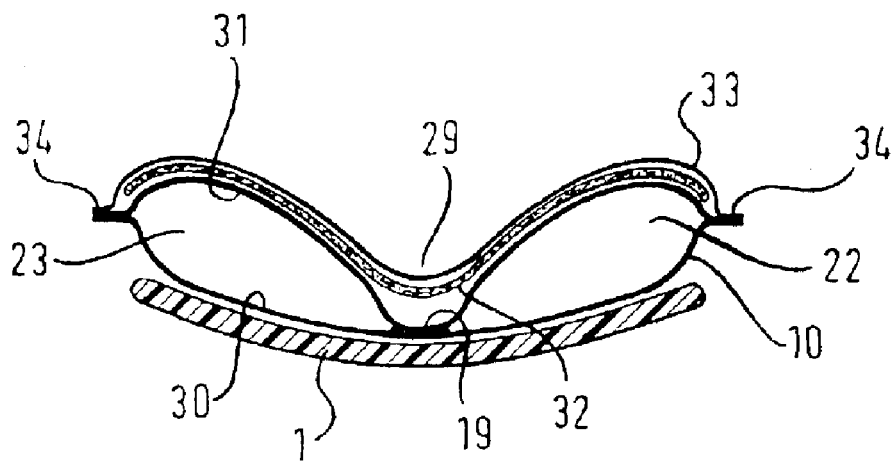
FIG. 6 shows a section through the arrangement according to FIG. 4 along line VI—VI.

FIG. 6 shows a section along line VI—VI from FIG. 4. The section, therefore, extends in the region in which the lines 20 and 21 meet, where also the ankle bone of the fitted ankle brace is situated. The there provided spot welds 19 (or the converged welds seams 27 and 28 in FIG. 5) result in the recess 29 into which an ankle bone is able to project without there being subjected to any special pressure. FIG. 6 also shows the arm 1 and the thereto attached cushioning chamber 10 in which the two walls 30 and 31 of the cushioning chamber 10 are joined owing to the spot weld 19 (corresponding to converging of the welds seams 27 and 28 in FIG. 5). It can also be seen from FIG. 6 that the cushioning chamber 10 is covered on one side by a soft cover 32 which is held in its position on the cushioning chamber 10 by the retaining foil 33. For this purpose, the retaining foil 33 is welded at its edge 34 to the edge of the cushioning chamber 10. In this design, therefore, the retaining foil 33 is in contact with the leg of the wearer of the ankle brace.

Figure 7:
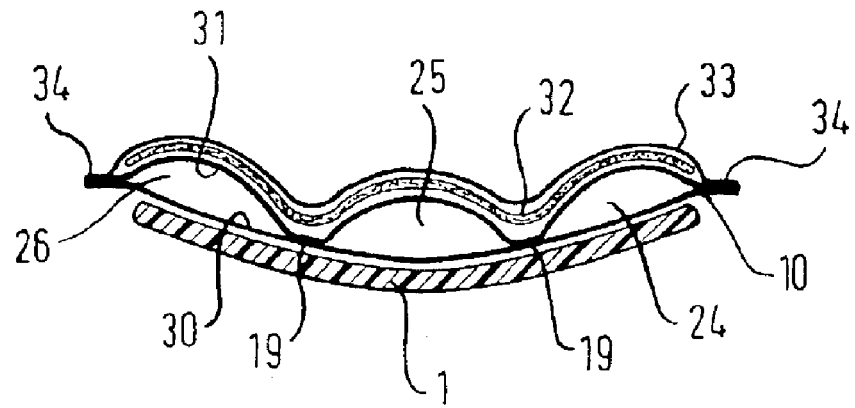
FIG. 7 shows a section through the arrangement according to FIG. 4 along line VII—VII.

The arrangement of the spot weld 19 results, next to the spot weld 19, in the two subchambers 22 and 23 which, because of the longitudinal subdivision of the common chamber space by the two lines 20 and 21, are continued into the subchambers 24, 25 and 26 (see FIG. 4 and FIG. 7).

FIG. 7 shows a section along line VII—VII from FIG. 4 which is broadly identical to the representation shown in FIG. 6, but with the modification that the section VII—VII extends through the region of the subchambers 24, 25 and 26, which are in communication with the common chamber space 18 and which are supplied with air via the supply channel 35.

What is claimed is:

1. Ankle brace with two arms 1, 2 extending over the ankle bones along the lower leg, said arms 1, 2 being joined under the foot by a flexible connecting member 2 and being provided with cushioning chambers 10, 12 containing a fluid, characterized in that each arm 1, 2 of the brace is provided with a single cushioning chamber 10, 12 with a longitudinal subdivision 20, 21; 27, 28, said longitudinal subdivision 20, 21; 27, 28 forming a zone of reduced expandability in the region of the ankle bone and therefore forming opposite the ankle bone a recess 29 which receives the latter, and in that the connecting member 3 is made of a material of such tensile elasticity that, during walking and the accompanying rolling of the foot as well as rhythmic pumping of the cushioning chambers 10, 12, said connecting member 3 is intermittently lengthened and shortened.

2. Ankle brace according to claim 1, characterized in that the longitudinal subdivision is formed by connections disposed between opposite walls 31, 31 of each cushioning chamber, said connections extending along the longitudinal subdivision.

3. Ankle brace according to claim 2, characterized in that the connections are formed by welding.

4. Ankle brace according to claim 3, characterized in that the connections are formed by series-arranged spot welds 19.

5. Ankle brace according to claim 3, characterized in that the connections are formed by welds seams 27, 28.

6. Ankle brace according to claim 2, characterized in that two lines 20, 21 of connections are provided, said lines extending in a V-shape such that the two lines meet in the region of the ankle bone and splay so wide apart towards the knee that, starting from the region of the ankle bone, two subchambers 22, 23 are formed next to the ankle bone and three juxtaposed subchambers 24, 25, 26 are formed in the transition of the lines towards the knee, the cross section of said three juxtaposed subchambers in the inflated state being decreasingly smaller than the cross section of each of the two subchambers 22, 23 in the region of the ankle bone.

* * * * *